United States Patent
He et al.

(10) Patent No.: US 11,813,499 B1
(45) Date of Patent: Nov. 14, 2023

(54) APPARATUS AND METHOD FOR AUTOMATICALLY ADJUSTING EXERCISE PRESCRIPTION BASED ON EXERCISE HEART RATE

(71) Applicant: RPLUSHEALTH LIMITED, Grand Cayman (KY)

(72) Inventors: Chunshui He, Chengdu (CN); Xi Chen, Chengdu (CN); Jiang Huang, Chengdu (CN); Fengming Yang, Chengdu (CN); Chi Lei, Chengdu (CN)

(73) Assignee: RPLUSHEALTH LIMITED, Grand Cayman (KY)

( * ) Notice: Subject to any disclaimer, the term of this patent is extended or adjusted under 35 U.S.C. 154(b) by 0 days.

(21) Appl. No.: 18/083,454

(22) Filed: Dec. 16, 2022

(51) Int. Cl.
*A63B 24/00* (2006.01)
*G16H 20/30* (2018.01)
*A63B 71/06* (2006.01)

(52) U.S. Cl.
CPC ...... *A63B 24/0075* (2013.01); *A63B 71/0622* (2013.01); *G16H 20/30* (2018.01); *A63B 2024/0068* (2013.01); *A63B 2071/063* (2013.01); *A63B 2071/0638* (2013.01); *A63B 2230/067* (2013.01)

(58) Field of Classification Search
CPC ............ A63B 24/0075; A63B 71/0622; A63B 2024/0068; A63B 2071/063; A63B 2071/0638; A63B 2230/067; G16H 20/30
See application file for complete search history.

(56) References Cited

U.S. PATENT DOCUMENTS

| | | | |
|---|---|---|---|
| 2013/0339409 A1* | 12/2013 | Kallio | G06F 1/163 600/529 |
| 2014/0277633 A1* | 9/2014 | Flaction | G06V 40/25 700/91 |
| 2015/0258415 A1* | 9/2015 | Trivedi | G09B 19/0038 700/91 |
| 2016/0213976 A1* | 7/2016 | So | A63B 71/0622 |
| 2017/0011210 A1* | 1/2017 | Cheong | A61B 5/681 |
| 2020/0014967 A1* | 1/2020 | Putnam | H04M 1/72409 |
| 2020/0015736 A1* | 1/2020 | Alhathal | A61B 5/11 |

* cited by examiner

*Primary Examiner* — Malina D. Blaise

(57) ABSTRACT

The present disclosure relates to an apparatus and method for automatically adjusting an exercise prescription based on an exercise heart rate. The apparatus includes: a heart rate detection device, configured to detect a resting heart rate and a user's real-time exercise heart rate; an exercise movement library, configured to store various exercise instruction video and audio, and provide movement guidance for the user; an exercise guidance module, configured to retrieve and display movement video and audio from the exercise movement library to the user; and a central processing unit (CPU), configured to acquire the resting heart rate and the user's real-time exercise heart rate, calculate an effective exercise target heart rate range based on the resting heart rate, determine whether the real-time exercise heart rate falls within the effective exercise target heart rate range.

10 Claims, 1 Drawing Sheet

APPARATUS AND METHOD FOR AUTOMATICALLY ADJUSTING EXERCISE PRESCRIPTION BASED ON EXERCISE HEART RATE

CROSS REFERENCE TO RELATED APPLICATION

This patent application claims the benefit and priority of Chinese Patent Application No. 202210422821.9, filed on Apr. 21, 2022, the disclosure of which is incorporated by reference herein in its entirety as part of the present application.

TECHNICAL FIELD

The present disclosure relates to the field of heart rate monitoring, and in particular, to an apparatus and method for automatically adjusting an exercise prescription based on an exercise heart rate.

BACKGROUND ART

Sports and fitness have gradually become an essential need in people's lives with improved living standards, and exercise is more critical for sub-healthy and chronic disease groups. Many scientific studies have confirmed and recommended that scientifically effective exercise can help patients manage their sub-health conditions and improve cardiopulmonary endurance, especially for the three high (hyperglycemia, hyperlipidemia, and hypertension) disease states has also been significantly improved. Such has big help and significant positive effect on blood sugar control, blood pressure and lipid reduction. However, in real life, because most people don't know how to start their exercise or haven't had exercise habit before, their exercise always can't reach the effective exercise heart rate range, or excessive exercise, which not only makes the effect of exercise significantly reduced, but also easy to cause sports injuries. On the other hand, the traditional in-person training making time is economically costly. So, the Telerehabilitation APP can bring convenience to such people.

Scientific and practical exercise prescription formulation is the core of APP home rehabilitation; only accurate exercise prescription formulation can ensure the effectiveness and safety of chronic disease rehabilitation.

Based on the formulation of exercise prescriptions, most users do not know how to carry out effective and safe exercise; personalized exercise instruction video for users' diseases can effectively help users solve this problem.

For users, the safety the effectiveness of exercise is the majority point for the entire exercise process. The intensity of exercise can be monitored in real-time by monitoring exercise heart rate.

There is a lack of an objective evaluation system to determine the influence of a specific exercise movement guidance on the individual heart rate. So the combination of the exercise instruction video, the target heart rate set by the course and the exercise prescription may be different. Therefore, the heart rate and exercise intensity during exercise can be adjusted by adjusting the intensity of exercise movement.

For users, they don't know how to make adjustments, so we provide a device that automatically adjusts the exercise prescription based on the feedback from patients during exercising to solve this problem.

SUMMARY

An objective of the present disclosure is to provide an apparatus and method for automatically adjusting an exercise prescription based on an exercise heart rate to match a more accurate exercise prescription for a user.

In order to achieve the above objective, the present disclosure provides the following technical solutions:

An apparatus for automatically adjusting an exercise prescription based on an exercise heart rate is provided. The apparatus includes:

a heart rate detection device, configured to detect a resting heart rate and a user's real-time exercise heart rate;

an exercise movement library, configured to store various exercise instruction video and audio, and provide movement guidance for the user;

an exercise guidance module, configured to retrieve and display movement video and audio from the exercise movement library to the user; and a central processing unit (CPU), configured to acquire the resting heart rate and the user's real-time exercise heart rate, calculate an effective exercise target heart rate range based on the resting heart rate, determine whether the real-time exercise heart rate falls within the effective exercise target heart rate range, and if the real-time exercise heart rate is beyond the effective exercise target heart rate range, remind the user through the exercise guidance module.

The CPU is further configured to: if the user's real-time exercise heart rate is beyond the effective exercise target heart rate range, adjust a playback rate of exercise instruction video or audio in the exercise guidance module.

Optionally, the heart rate detection device may be a heart rate monitor, a sports watch, or a sports band.

Optionally, the following formula is used to calculate the effective exercise target heart rate range based on the resting heart rate:

Target exercise heart rate range=(Maximum heart rate−Resting heart rate)×Exercise intensity+Resting heart rate Optionally, the effective exercise target heart rate range may be set by a doctor.

Optionally, that the CPU is further configured to: if the user's real-time exercise heart rate is beyond the effective exercise target heart rate range, adjust the playing speed of the video or the audio in the exercise guidance module may specifically include the following steps:

if the real-time exercise heart rate is higher than an effective exercise target heart rate interval and exceeds a preset time, transmitting, by the heart rate detection device, the acquired heart rate to the CPU immediately, and performing, by the CPU, first speed level reduction on the guidance video or audio through the exercise guidance module; and if the heart rate detection device detects that the heart rate is still higher than the effective exercise target heart rate interval and exceeds the preset time after the first speed level reduction, performing, by the CPU, second speed level reduction on the guidance video or audio;

if the heart rate is still higher than the effective exercise target heart rate range after the two consecutive exercise intensity adjustments, automatically stopping the movement, transmitting the heart rate at this moment to the CPU and a doctor client, and matching, by the CPU, a new movement from the exercise movement library, or manually adjusting, by the doctor, an exercise prescription;

if the real-time exercise heart rate is lower than an effective exercise target heart rate interval and exceeds the preset time, transmitting, by the heart rate detection device, the acquired heart rate to the CPU immediately, and performing, by the CPU, first speed level increase on the guidance video or audio through the exercise guidance module; and if the heart rate detection device detects that the heart rate is still lower than the effective exercise target heart rate interval and exceeds the preset time after the first speed level increase, adjusting, by the CPU, the playing speed of the guidance video or audio to level II+; and if the exercise heart rate is still lower than the effective exercise target heart rate range after the two consecutive exercise intensity adjustments, automatically skipping, by a system, the movement, transmitting the heart rate at this moment to the CPU and the doctor client, and matching, by the CPU, a new movement from the exercise movement library, or manually adjusting, by the doctor, the exercise prescription.

Optionally, the CPU is further configured to eliminate, based on exercise information obtained after training is finished, the movement for which the exercise heart rate is still beyond the effective exercise target heart rate range after the two exercise intensity adjustments during current exercise, match a new movement of a same type, and perform a speed level adjustment to match a new exercise prescription.

Based on the foregoing apparatus in the present disclosure, the present disclosure further provides a method for automatically adjusting an exercise prescription based on an exercise heart rate. The method is applied to the foregoing apparatus and includes:

obtaining a resting heart rate and a user's real-time exercise heart rate;

constructing an exercise movement library, where the exercise movement library is configured to store various exercise instruction video and audio, and provide movement guidance for the user;

retrieving video and audio from the exercise movement library to the user;

calculating an effective exercise target heart rate range based on the resting heart rate; and determining whether the real-time exercise heart rate falls within the effective exercise target heart rate range, and if the real-time exercise heart rate is beyond the effective exercise target heart rate range, reminding the user and adjusting a playback rate of exercise instruction video or audio.

Optionally, the following formula is used to calculate the effective exercise target heart rate range based on the resting heart rate:

Target exercise heart rate range=(Maximum heart rate−Resting heart rate)×Exercise intensity+Resting heart rate Optionally, adjusting the playing speed of the video or the audio in the exercise guidance module may specifically include the following steps:

if the real-time exercise heart rate is higher than an effective exercise target heart rate interval and exceeds a preset time, transmitting, by a heart rate detection device, the acquired heart rate to a CPU immediately, and performing, by the CPU, first speed level reduction on the guidance video or audio through an exercise guidance module; and if the heart rate detection device detects that the heart rate is still higher than the effective exercise target heart rate interval and exceeds the preset time after the first speed level reduction, performing, by the CPU, second speed level reduction on the guidance video or audio;

if the heart rate is still higher than the effective exercise target heart rate range after the two consecutive exercise intensity adjustments, automatically stopping the movement, transmitting the heart rate at this moment to the CPU and a doctor client, and matching, by the CPU, a new movement from the exercise movement library, or manually adjusting, by the doctor, an exercise prescription;

if the real-time exercise heart rate is lower than an effective exercise target heart rate interval and exceeds the preset time, transmitting, by the heart rate detection device, the acquired heart rate to the CPU immediately, and performing, by the CPU, first speed level increase on the guidance video or audio through the exercise guidance module; and if the heart rate detection device detects that the heart rate is still lower than the effective exercise target heart rate interval and exceeds the preset time after the first speed level increase, adjusting, by the CPU, the playing speed of the guidance video or audio to level II+; and if the exercise heart rate is still lower than the effective exercise target heart rate range after the two consecutive exercise intensity adjustments, automatically skipping, by a system, the movement, transmitting the heart rate at this moment to the CPU and the doctor client, and matching, by the CPU, a new movement from the exercise movement library, or manually adjusting, by the doctor, the exercise prescription.

Optionally, the method may further include:

eliminating, based on exercise information obtained after training is finished, a movement for which the exercise heart rate is still beyond the effective exercise target heart rate range after two exercise intensity adjustments during current exercise, matching a new movement of a same type, and performing a speed level adjustment to match a new exercise prescription.

Based on specific embodiments provided in the present disclosure, the present disclosure has the following technical effects:

In the present disclosure, the resting heart rate of the user is detected by the heart rate detection device, to determine the target exercise heart rate range of the user. In this way, a safe and effective target heart rate range is obtained. Then, the target heart rate range is used to determine the heart rate of the user in an exercise cycle. This can effectively improve an exercise effect without exceeding a physical bearing capacity of the user. Safety and high efficiency are implemented. In the present disclosure, it is detected immediately whether the exercise heart rate matches the target heart rate range to resolve the problem that an exercise prescription pushed by a self-energy engine is not accurate enough, and a more accurate exercise prescription can be matched for the patient. In the present disclosure, the heart rate detection device detects changes in an instantaneous heart rate during the exercise of the user immediately, real-time determining and analysis are performed, and the exercise intensity is further adjusted. If the heart rate is still lower than or higher than the target heart rate interval and exceeds the preset time after two exercise intensity adjustments, the exercise is automatically stopped. This can effectively prevent an ineffective exercise effect of the user due to week exercise intensity or body injuries due to strong exercise intensity immediately. The present disclosure can ensure efficient and safe exercise in different environments. The health status, environments, seasons, and mood in different periods have impact on an exercise amount. For example, under external conditions such as cold, hot weather, or an insolation environment, the exercise intensity and exercise duration should be correspondingly reduced, and the heart rate should also be correspondingly reduced. To ensure exercise effectiveness and safety, the target heart rate range should also be flexibly changed based on specific situations, and the exercise safety can be better ensured by matching the real-time exercise heart rate immediately through real-time exercise.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

DETAILED DESCRIPTION OF THE EMBODIMENTS

The technical solutions in the embodiments of the present disclosure will be described below clearly and completely with reference to the accompanying drawings in the embodiments of the present disclosure. Apparently, the described embodiments are merely some rather than all of the embodiments of the present disclosure. All other embodiments obtained by a person of ordinary skill in the art based on the embodiments of the present disclosure without creative efforts shall fall within the protection scope of the present disclosure.

An objective of the present disclosure is to provide an apparatus and method for automatically adjusting an exercise prescription based on an exercise heart rate to match a more accurate exercise prescription for a user.

To make the above-mentioned objective, features, and advantages of the present disclosure clearer and more comprehensible, the present disclosure will be further described in detail below in conjunction with the accompanying drawings and specific embodiments.

The apparatus for automatically adjusting an exercise prescription based on an exercise heart rate provided in the present disclosure is composed of a doctor client, a patient client, and a server. The client serves as both an exercise rehabilitation execution platform and a data acquisition tool. The server serves as both a machine learning database and a data processing platform. A real-time exercise heart rate of a patient acquired by the patient client is transmitted to the server and synchronized to the doctor client such that a system can recognize the change of the heart rate of the patient and adjust a playback rate of exercise instruction video or audio to adjust exercise intensity of the patient. If the exercise heart rate of the patient is beyond a target heart rate range for specific duration, the system automatically terminates exercise. After the exercise is completed, data such as the heart rate and a movement frequency during the exercise is transmitted to the server for analysis, to match a more accurate exercise prescription for the patient.

Figure 1:
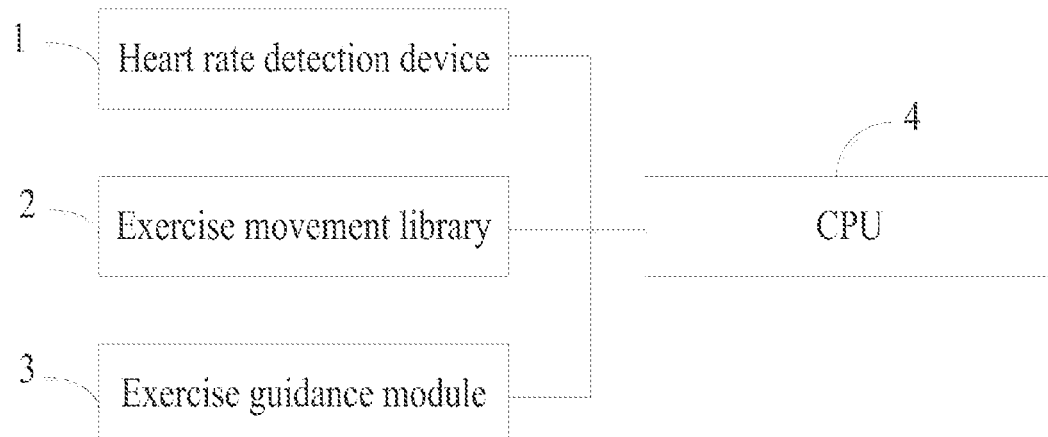
FIG. 1 is a schematic structural diagram of an apparatus for automatically adjusting an exercise prescription based on an exercise heart rate according to an embodiment of the present disclosure.

FIG. 1 is a schematic structural diagram of an apparatus for automatically adjusting an exercise prescription based on an exercise heart rate according to an embodiment of the present disclosure. As shown in FIG. 1, the apparatus includes a heart rate detection device 1, an exercise movement library 2, an exercise guidance module 3, and a CPU 4.

The heart rate detection device 1 is configured to detect a resting heart rate and a user's real-time exercise heart rate.

The exercise movement library 2 is configured to store various exercise instruction video and audio, and provide movement guidance for the user.

The exercise guidance module 3 is configured to retrieve and display movement video and audio from the exercise movement library to the user.

The CPU 4 is configured to acquire the resting heart rate and the user's real-time exercise heart rate, calculate an effective exercise target heart rate range based on the resting heart rate, determine whether the real-time exercise heart rate falls within the effective exercise target heart rate range, and if the real-time exercise heart rate is beyond the effective exercise target heart rate range, remind the user through the exercise guidance module.

The CPU 4 is further configured to: if the user's real-time exercise heart rate is beyond the effective exercise target heart rate range, adjust a playback rate of exercise instruction video or audio in the exercise guidance module.

Specifically, the heart rate detection device may be a heart rate monitor, a sports watch, or a sports band.

The following formula is used to calculate the effective exercise target heart rate range based on the resting heart rate:

Target exercise heart rate range=(Maximum heart rate−Resting heart rate)×Exercise intensity+Resting heart rate The maximum heart rate is 220 minus an age. The exercise intensity is 40% to 90% of a heart rate reserve (HRR). When the exercise intensity is 40% to 60% of the HRR, the exercise intensity is medium exercise intensity. The user takes aerobic exercise for determined exercise duration based on guidance of the exercise movement library. The heart rate detection device detects an instantaneous heart rate of the user during exercise during the aerobic exercise immediately, and transmits the detected exercise heart rate to the CPU. The effective exercise target heart rate range may alternatively be manually set by a doctor.

That the CPU is further configured to: if the user's real-time exercise heart rate is beyond the effective exercise target heart rate range, adjust the playing speed of the video or the audio in the exercise guidance module may specifically include the following steps:

If the real-time exercise heart rate is higher than an effective exercise target heart rate interval and exceeds a preset time, the heart rate detection device transmits the acquired heart rate to the CPU immediately, and the CPU performs first speed level reduction on the guidance video or audio through the exercise guidance module. If the heart rate detection device detects that the heart rate is still higher than the effective exercise target heart rate interval and exceeds the preset time after the first speed level reduction, the CPU performs second speed level reduction on the guidance video or audio.

If the heart rate is still higher than the effective exercise target heart rate range after the two consecutive exercise intensity adjustments, the movement is automatically stopped, the heart rate at this moment is transmitted to the CPU and a doctor client, and the CPU matches a new movement from the exercise movement library, or the doctor manually adjusts an exercise prescription.

If the real-time exercise heart rate is lower than an effective exercise target heart rate interval and exceeds the preset time, the heart rate detection device transmits the acquired heart rate to the CPU immediately, and the CPU performs first speed level increase on the guidance video or audio through the exercise guidance module. If the heart rate detection device detects that the heart rate is still lower than the effective exercise target heart rate interval and exceeds the preset time after the first speed level increase, the CPU adjusts the playing speed of the guidance video or audio to level II+.

If the exercise heart rate is still lower than the effective exercise target heart rate range after the two consecutive exercise intensity adjustments, a system automatically skips the movement, the heart rate at this moment is transmitted to the CPU and the doctor client, and the CPU matches a new movement from the exercise movement library, or the doctor manually adjusts the exercise prescription.

The CPU is further configured to eliminate, based on exercise information obtained after training is finished, the movement for which the exercise heart rate is still beyond the effective exercise target heart rate range after the two exercise intensity adjustments during current exercise, match a new movement of a same type, and perform a speed level adjustment to match a new exercise prescription.

The technical solution of the present disclosure is described in detail below with reference to a specific example.

First, a heart rate detection device detects a resting heart rate of a user by using a 3 minute step test. Then, a target exercise heart rate range is determined based on the detected resting heart rate.

The following formula is used to calculate the target exercise heart rate range: Target exercise heart rate range=(Maximum heart rate−Resting heart rate)×Exercise intensity+Resting heart rate, where the maximum heart rate is 220 minus an age. For example, the user is 30 years old. The resting heart rate of 60 is detected by using the 3 minute step test. Exercise duration when the heart rate reaches 60% to 90% of the HRR at high exercise intensity is 1 minute, which is 2 times actual exercise duration. A remaining aerobic exercise amount is calculated as follows: Target exercise heart rate range=(Maximum heart rate−Resting heart rate)× High intensity (60% to 90%)+Resting heart rate=(190−60)× (60% to 90%)+60=138 to 177 beats per minute. In other words, the target heart rate range of the user in the duration is 138 to 177 beats per minute.

Exercise duration when the heart rate reaches 40% to 60% of the HRR at medium exercise intensity is 1 minute, which is actual exercise duration. A remaining aerobic exercise amount is calculated as follows: Target exercise heart rate range=(Maximum heart rate−Resting heart rate)×Medium intensity (40% to 60%)+Resting heart rate=(190−60)×(40% to 60%)+60=112 to 138 beats per minute. In other words, the target heart rate range of the user in the duration is 112 to 138 beats per minute. For another example, a safe target heart rate for middle-aged and elderly or chronically ill people ranges between (170-Age) and (180-Age). For example, an aerobic heart rate of a 70-year-old patient is generally controlled between (170-70) and (180-70), namely, between 100 and 110 beats per minute. For patients who start to use exercise intervention, it is safer to apply a safety factor of 0.9. For example, the safe target heart rate of the 70-year-old patient should be controlled between (170-70)×0.9 and (180-70)×0.9, namely, between 90 and 99 beats per minute at first.

Based on the foregoing method for determining the target heart rate range, the present disclosure provides an apparatus (namely, an exercise guidance module) that can automatically match an exercise heart rate for the user, including a CPU, and a heart rate detection device, an exercise movement library, an exercise detection module, an exercise guidance module, and a step that are connected to the CPU.

Worn on the user, the heart rate detection device may be a heart rate monitor, a sports watch, or a sports band, and is configured to detect the resting heart rate and the heart rate of the user during exercise.

The exercise movement library is configured to store various exercise instruction video and provide movement guidance for the user, including warming up before exercise, movement recommendation during the exercise, and stretching after the exercise.

The step is configured to assist the user to perform the 3 minute step test. The heart rate detection device obtains the resting heart rate, which is used as an evaluation standard for determining cardiopulmonary endurance of the user.

The CPU is configured to acquire the resting heart rate and the heart rate of the user during exercise, set a safe and effective exercise target heart rate range based on the resting heart rate of the user, determine whether the heart rate of the user during exercise is effective, and if the exercise heart rate is beyond the effective exercise target heart rate range, remind the user through the movement heart rate matching apparatus.

The CPU adjusts only the speed at which a training movement is performed in a training process during the exercise, and does not adjust stretching, arranging, warming up, and functional movements.

After the exercise starts, the CPU detects the exercise heart rate. If the heart rate detection device detects that the heart rate is higher than a target heart rate range for 10s, the heart rate detection device transmits information to the CPU.

The exercise guidance module is a device through which the CPU matches the movement heart rate based on the exercise heart rate detected immediately. The CPU classifies the playing speed of an movement guidance video or audio into five levels: level I, level I-, level II-, level I+, and level II+, which may specifically be 0.6×, 0.8×, 1.0×, 1.2×, and 1.4×.

An initial playing speed is set to level I. The heart rate detection device transmits the acquired heart rate to the CPU immediately. If the current heart rate matches the target heart rate, no adjustment is performed.

If the real-time exercise heart rate is higher than an target heart rate interval and exceeds a preset time, the heart rate detection device transmits the acquired heart rate to the CPU immediately, and the CPU adjusts the playing speed of the guidance video or audio to level I-. If the heart rate detection device detects that the heart rate is still lower than the target heart rate interval and exceeds the preset time after the speed is adjusted, the CPU adjusts the playing speed of the guidance video or audio to level II-. If the heart rate is still higher than the target heart rate range for two minutes after the two consecutive exercise intensity adjustments, to ensure exercise safety of the patient, the movement is automatically stopped, data is transmitted to the CPU and a doctor client, and the system automatically matches a new movement for the patient, or the doctor manually adjusts an exercise prescription of the patient.

If the real-time exercise heart rate is lower than the target heart rate interval and exceeds the preset time, the heart rate detection device transmits the acquired heart rate to the CPU immediately, and the CPU adjusts the playing speed of the guidance video or audio to level I+. If the heart rate is still lower than the target heart rate interval and exceeds the preset time after the speed is adjusted, the CPU adjusts the playing speed of the guidance video or audio to level II+. If the heart rate is still lower than the target heart rate range after the two consecutive speed adjustments, the system automatically skips the movement and matches a new movement for the patient, and data is also transmitted to the doctor client, and the doctor may alternatively manually adjust the exercise prescription of the patient.

After a single movement is performed for a specific number of times, a next movement starts from the level I speed.

After the training is finished, the system automatically uploads current exercise information to the CPU, and the CPU eliminates the movement for which the exercise heart rate is beyond the exercise heart rate range after the two exercise intensity adjustments during the current exercise, matches a new movement of a same type, and performs a speed level adjustment to match a new exercise prescription.

Figure 2:
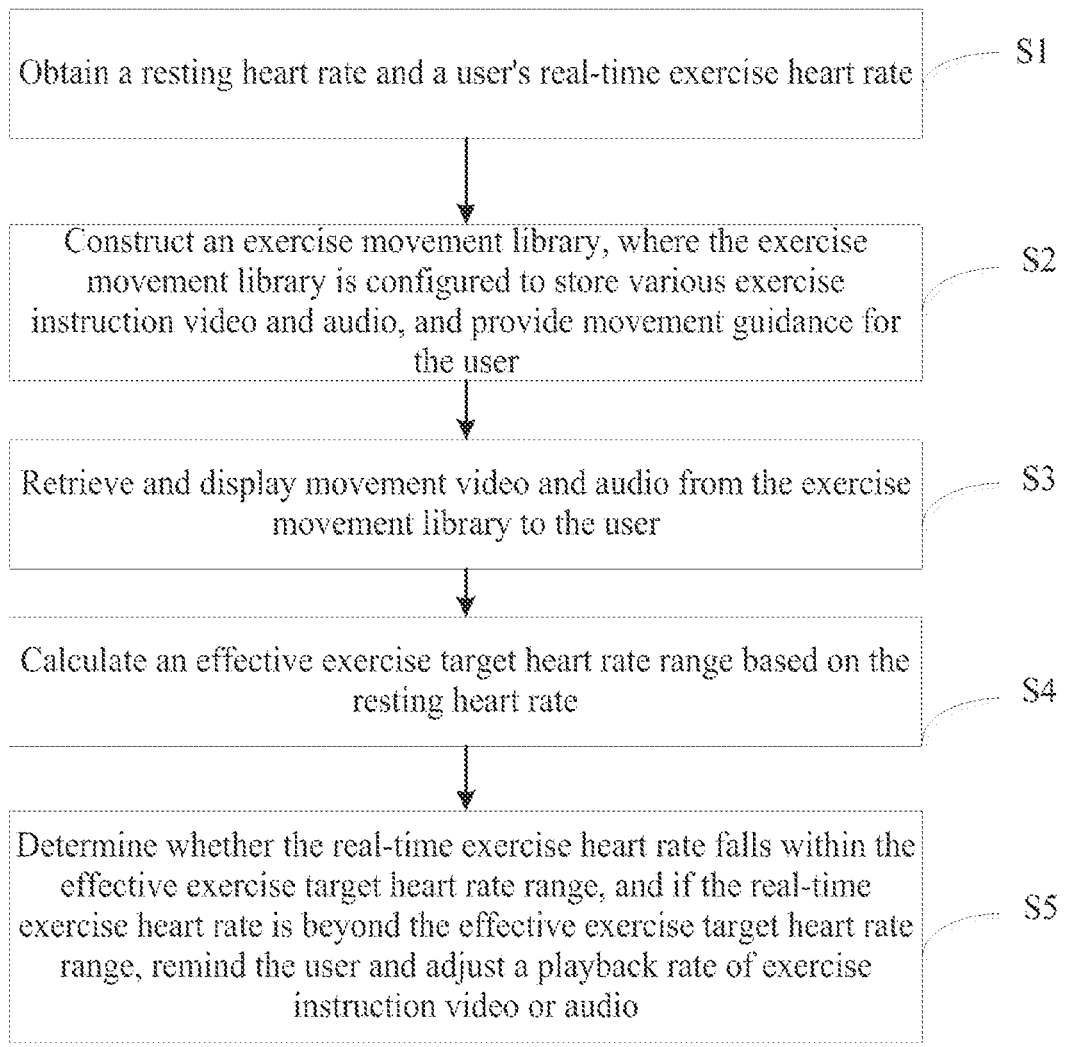
FIG. 2 is a flowchart of a method for automatically adjusting an exercise prescription based on an exercise heart rate according to an embodiment of the present disclosure.

As shown in FIG. 2, the method includes:

Step S1: Obtain a resting heart rate and a user's real-time exercise heart rate.

Specifically, the resting heart rate and the user's real-time exercise heart rate are obtained by a heart rate monitor, a sports watch, or a sports band.

Step S2: Construct an exercise movement library, where the exercise movement library is configured to store various exercise instruction video and audio, and provide movement guidance for the user.

Step S3: Retrieve and display movement video and audio from the exercise movement library to the user.

Step S4: Calculate an effective exercise target heart rate range based on the resting heart rate.

Specifically, the calculation formula is as follows:

Target exercise heart rate range=(Maximum heart rate− Resting heart rate)×Exercise intensity+Resting heart rate Step S5: Determine whether the real-time exercise heart rate falls within the effective exercise target heart rate range, and if the real-time exercise heart rate is beyond the effective exercise target heart rate range, remind the user and adjust a playback rate of exercise instruction video or audio.

Specifically, that the playing speed of the video or audio is adjusted may specifically include the following steps:

If the real-time exercise heart rate is higher than an effective exercise target heart rate interval and exceeds a preset time, a heart rate detection device transmits the acquired heart rate to a CPU immediately, and the CPU adjusts the playing speed of the guidance video or audio to level I- through an exercise guidance module. If the heart rate detection device detects that the heart rate is still higher than the effective exercise target heart rate interval and exceeds the preset time after the speed is adjusted, the CPU adjusts the playing speed of the guidance video or audio to level-II.

If the heart rate is still higher than the effective exercise target heart rate range after the two consecutive exercise intensity adjustments, the movement is automatically stopped, the heart rate at this moment is transmitted to the CPU and a doctor client, and the CPU matches a new movement from the exercise movement library, or the doctor manually adjusts an exercise prescription.

If the real-time exercise heart rate is lower than an effective exercise target heart rate interval and exceeds the preset time, the heart rate detection device transmits the acquired heart rate to the CPU immediately, and the CPU adjusts the playing speed of the guidance video or audio to level I+ through the exercise guidance module. If the heart rate detection device detects that the heart rate is still lower than the effective exercise target heart rate interval and exceeds the preset time after the speed is adjusted, the CPU adjusts the playing speed of the guidance video or audio to level II+.

If the exercise heart rate is still lower than the effective exercise target heart rate range after the two consecutive exercise intensity adjustments, a system automatically skips the movement, the heart rate at this moment is transmitted to the CPU and the doctor client, and the CPU matches a new movement from the exercise movement library, or the doctor manually adjusts the exercise prescription.

Each embodiment of the present specification is described in a progressive manner, each embodiment focuses on the difference from other embodiments, and the same and similar parts between the embodiments may refer to each other.

In this specification, some specific embodiments are used for illustration of the principles and implementations of the present disclosure. The description of the foregoing embodiments is used to help illustrate the method of the present disclosure and the core ideas thereof. In addition, persons of ordinary skill in the art can make various modifications in terms of specific implementations and the scope of application in accordance with the ideas of the present disclosure. In conclusion, the content of this specification shall not be construed as limitations to the present disclosure.

What is claimed is:

1. An apparatus for rehabilitative training, the apparatus comprising:
   a server, the server comprising an exercise movement library, wherein the exercise movement library stores various exercise instruction video and audio, and provides movement guidance for the user; wherein a playback speed of the various exercise instruction video and audio is classified by the server to five levels: level II-, level I-, level I, level I+, and level II+ respectively responding to 0.6×, 0.8×, 1.0×, 1.2×, and 1.4×;
   a heart rate detection device configured to detect a resting heart rate and a real-time exercise heart rate of a user and transmit the resting heart rate and the real-time exercise heart rate to the server; and
   an exercise guidance device configured to retrieve an exercise instruction video and audio with an initial playback speed of level I from the exercise movement library and display the exercise instruction video and audio to the user,
   wherein the server is configured to:
   calculate an effective exercise target heart rate range based on the resting heart rate;
   determine whether the real-time exercise heart rate falls within the effective exercise target heart rate range; and
   adjust the exercise instruction video and audio based on the determined result, wherein when the real-time exercise heart rate is higher than an effective exercise target heart rate interval and exceeds a preset time, a first speed level reduction to level I- is performed on the exercise instruction video and audio presented on the exercise guidance device;
   when the real-time heart rate is still higher than the effective exercise target heart rate interval and exceeds the preset time after the first speed level reduction, a second speed level reduction to level II- is performed on the exercise instruction video and audio presented on the exercise guidance device;
   when the real-time heart rate is still higher than the effective exercise target heart rate range after the two consecutive speed level reductions, play of the exercise instruction video and audio is stopped, and a current heart rate is transmitted to a doctor client and a new exercise instruction video and audio, matching a current heart rate with an identical type of the exercise instruction video and audio from the exercise movement library, is selected and the new exercise instruction video and audio is transmitted to the exercise guidance device for playback, or a new exercise instruction video and audio, matching the current heart rate with the identical type of the exercise instruction video and audio, is selected by a doctor and is transmitted to the exercise guidance device for playback; or when the real-time exercise heart rate is less than the effective exercise target heart rate interval and exceeds the preset time, a first speed level increase to level I+ is performed on the exercise instruction video and audio presented on the exercise guidance device;

when the real-time heart rate is less than the effective exercise target heart rate interval and exceeds the preset time after the first speed level increase, a second speed level increase to level II+ is performed on the exercise instruction video and audio presented on the exercise guidance device;

when the real-time heart rate is still less than the effective exercise target heart rate range after the two consecutive speed level increases, play of the exercise instruction video and audio is stopped, and a current heart rate is transmitted to the doctor client and a new exercise instruction video and audio, matching the current heart rate with the identical type of the exercise instruction video and audio from the exercise movement library, is selected and the new exercise instruction video and audio is transmitted to the exercise guidance device for playback, or a new exercise instruction video and audio, matching the current heart rate with the identical type of the exercise instruction video and audio, is selected by the doctor and is transmitted to the exercise guidance device for playback.

2. The apparatus of claim 1, wherein the heart rate detection device is a heart rate monitor, a sports watch, or a sports band.

3. The apparatus of claim 1, wherein the following formula is used to calculate the effective exercise target heart rate range based on the resting heart rate:

target exercise heart rate range=(maximum heart rate−resting heart rate)×exercise intensity+resting heart rate.

4. The apparatus of claim 1, wherein the effective exercise target heart rate range is set by a doctor.

5. The apparatus of claim 1, wherein the server is further configured to eliminate, based on exercise information obtained after training is finished, the movement for which the exercise heart rate is still beyond the effective exercise target heart rate range after the two exercise intensity adjustments during current exercise, match a new movement of a same type, and perform a speed level adjustment to match a new exercise prescription.

6. A method for rehabilitative training, the method comprising:

by a heart rate detection device, obtaining a resting heart rate and a real-time exercise heart rate of a user and transmitting the resting heart rate and the real-time exercise heart rate to a server, wherein the server comprises an exercise movement library and a processor, the exercise movement library stores various exercise instruction video or audio, and provides movement guidance for the user;

by an exercise guidance device, retrieving an exercise instruction video and audio with an initial playback speed of level I from the exercise movement library and displaying the exercise instruction video or audio to the user;

calculating, by the server, an effective exercise target heart rate range based on the resting heart rate; and determining, by the server, whether the real-time exercise heart rate falls within the effective exercise target heart rate range; and adjusting, by the server, the exercise instruction video and audio based on the determined result, wherein a playback speed of the exercise instruction video and audio is classified to five levels: level II-, level I-, level I, level I+, and level II+ respectively responding to 0.6×, 0.8×, 1.0×, 1.2×, and 1.4×; and wherein adjusting, by the server, the exercise instruction video and audio based on the determined result comprises:

when the real-time exercise heart rate is higher than an effective exercise target heart rate interval and exceeds a preset time, performing a first speed level reduction to level I- on the exercise instruction video and audio presented on the exercise guidance device;

when the real-time heart rate is still higher than the effective exercise target heart rate interval and exceeds the preset time after the first speed level reduction, performing a second speed level reduction to level II- on the exercise instruction video and audio presented on the exercise guidance device;

when the real-time heart rate is still higher than the effective exercise target heart rate range after the two consecutive speed level reductions, stopping play of the exercise instruction video and audio, and transmitting a current heart rate to a doctor client and selecting a new exercise instruction video and audio matching a current heart rate with an identical type of the exercise instruction video and audio from the exercise movement library and transmitting the new exercise instruction video and audio to the exercise guidance device for playback, or transmitting a new exercise instruction video and audio, selected by a doctor, matching the current heart rate with the identical type of the exercise instruction video and audio to the exercise guidance device for playback; or when the real-time exercise heart rate is less than the effective exercise target heart rate interval and exceeds the preset time, performing a first speed level increase to level I+ on the exercise instruction video and audio presented on the exercise guidance device;

when the real-time heart rate is less than the effective exercise target heart rate interval and exceeds the preset time after the first speed level increase, performing a second speed level increase to level II+ on the exercise instruction video and audio presented on the exercise guidance device;

when the real-time heart rate is still less than the effective exercise target heart rate range after the two consecutive speed level increases, stopping play of the exercise instruction video and audio, and transmitting a current heart rate to the doctor client and selecting a new exercise instruction video and audio matching the current heart rate with the identical type of the exercise instruction video and audio from the exercise movement library and transmitting the new exercise instruction video and audio to the exercise guidance device for playback, or transmitting a new exercise instruction video and audio, selected by the doctor, matching the current heart rate with the identical type of the exercise instruction video and audio to the exercise guidance device for playback.

7. The method of claim 6, wherein the following formula is used to calculate the effective exercise target heart rate range based on the resting heart rate:

target exercise heart rate range=(maximum heart rate−resting heart rate)×exercise intensity+resting heart rate.

8. The method of claim 6, further comprising:

eliminating, based on exercise information obtained after training is finished, a movement for which the exercise heart rate is still beyond the effective exercise target heart rate range after two exercise intensity adjustments during current exercise, matching a new movement of a same type, and performing a speed level adjustment to match a new exercise prescription.

9. The method of claim 6, wherein the heart rate detection device is a heart rate monitor, a sports watch, or a sports band.

10. The method of claim 6, wherein the effective exercise target heart rate range is set by a doctor.

* * * * *

UNITED STATES PATENT AND TRADEMARK OFFICE
CERTIFICATE OF CORRECTION

Page 1 of 1

PATENT NO. : 11,813,499 B1
APPLICATION NO. : 18/083454
DATED : November 14, 2023
INVENTOR(S) : Chunshui He et al.

It is certified that error appears in the above-identified patent and that said Letters Patent is hereby corrected as shown below:

On the Title Page

Item (30), Foreign Application Priority Data, please insert:
--Apr. 21, 2022 (CN).........................202210422821.9--

Signed and Sealed this
Twenty-fifth Day of February, 2025

Coke Morgan Stewart
*Acting Director of the United States Patent and Trademark Office*